United States Patent

Guggenheim et al.

Patent Number: 5,589,037
Date of Patent: Dec. 31, 1996

[54] METHOD FOR REMOVING TETRANITROMETHANE FROM NITRIC ACID

[75] Inventors: Thomas L. Guggenheim, Mt. Vernon, Ind.; Sharon M. Fukuyama, Parkersburg, W. Va.; Gregory L. Warner, Schenectady, N.Y.

[73] Assignee: General Electric Company, Pittsfield, Mass.

[21] Appl. No.: 547,516

[22] Filed: Oct. 24, 1995

[51] Int. Cl.⁶ ........................................................ B01D 3/34
[52] U.S. Cl. .................... 203/35; 159/DIG. 19; 203/49; 203/98; 423/394.2
[58] Field of Search .............................. 203/35, 49, 98, 203/DIG. 9; 423/394.2, 390; 159/DIG. 19, 16.1

[56] References Cited

U.S. PATENT DOCUMENTS

| | | | |
|---|---|---|---|
| 3,401,095 | 9/1968 | Saradzhev | 203/13 |
| 4,289,706 | 9/1981 | Fukasawa et al. | 260/369 |
| 4,713,232 | 12/1987 | Chin et al. | |

FOREIGN PATENT DOCUMENTS 57-156445   9/1982   Japan .

OTHER PUBLICATIONS

Yamato, O. Int. J. Radiat. Biol. Relat. Stud. Phys., Chem. Med. 1982/42(6), 661.

Sutton, H. C.; Seddon, W. A.; Sopchyshyn, F. C. Can. J. Chem. 1978, 56, 1961.

Sutton, H. C. J. Chem. Soc. Faraday 1 1975, 71, 2142.

Brown, L. H.; Geckler, R. D., "Research in Nitropolymers and their Application to solid smokeless Propellants" (no date available).

Harada, T.; Nishikido, N.; Morio, Y; Matuura, R. Bull. Chem. Soc. Jpn. 1981 4(9), 2592.

Mundy, R. A.; Gilbert, E. E. Report RAD-240.10, PI-557, ARLCD-TR-78027, AD-E400164, Order No. AD-A056244, Gov. Rep. Announce. Index (U>S.) 1978, 78(21), 250.

Isacs, N. S.; Abed, O. H. Tet. Lett. 1982, 23, 2799.

Frank, A. J.; Henglein, A. Berichte der Bunsen Gesellschaft 1976, 7, 393.

Kimura, M.; Ikeda, T.; Hara, N. Nippon Kagaku Karshi 1982, 3, 341.

Kumara, M.; Skukutani, M. Bull. Chem. Soc. Jap. 1979, 52, 2535.

Korsakov, V. G.; Kedrinskii, L. A. Elektrokhimiya 1976, 12, 1562.

*Primary Examiner*—Wayne Langel
*Assistant Examiner*—Karen Joyce

[57] ABSTRACT

Tetranitromethane and other polynitrated methanes can be effectively removed from otherwise substantially organic-free nitric acid streams through the addition of substantially organic-free concentrated sulfuric acid and by, optionally, performing secondary operations such as sparging the mixed acid stream with a gas such as nitric oxide or with an oil.

15 Claims, No Drawings

METHOD FOR REMOVING TETRANITROMETHANE FROM NITRIC ACID

BACKGROUND OF THE INVENTION

Tetranitromethane (TNM) is a common byproduct resulting from the nitration of many organic substances. TNM is a toxic material. TNM is also an oxidizer that can form a powerful explosive when mixed with combustible organic materials such as benzene, nitrobenzene, toluene, etc. For example, the presence of TNM has been held responsible for explosions in trinitrotoluene manufacturing facilities.

TNM can present other challenges in manufacturing facilities as it is very soluble in strong nitric acid, e.g., greater than about 30% by weight in 99% nitric acid, but not in 40% nitric acid (~0.5% by weight) or in 85% sulfuric acid(~0.8% by weight). Although TNM is soluble in concentrated nitric acid, it is difficult to separate from concentrated nitric acid.

Moreover, most nitration facilities require recycling of acids, e.g., sulfuric and nitric acids, to provide for an economical and environmentally sound process. The possibility of TNM concentrating in an acid recycle stream is real if a purge or destruction process is not implemented.

The present invention provides a process to safely and effectively remove and destroy TNM from a substantially pure concentrated nitric acid stream without also stripping a significant amount of the nitric acid desired for recycle.

SUMMARY OF THE INVENTION

The present invention relates to a process for removing tetranitromethane from a tetranitromethane-contaminated but otherwise substantially organic-free concentrated nitric acid stream, comprising the steps of (A) adding substantially organic-free concentrated sulfuric acid to the nitric acid stream to form a mixed acid stream that contains tetranitromethane, wherein the amount of sulfuric acid added is effective to render the tetranitromethane capable of removal from the mixed acid stream by sparging the mixture with air or with an inert gas; and (B) separating tetranitromethane from the mixed acid stream. The sulfuric acid is added in an amount effective to enable removal of the tetranitromethane by sparging the acid mixture with air or inert gas. The process allows removal, concentration and destruction of a significant portion the TNM that is being generated in the nitric acid stream, while minimizing the amount of nitric acid removed with the tetranitromethane.

DETAILED DESCRIPTION OF THE INVENTION

The process of the present invention has broad application to many nitration processes where TNM is generated in the nitric acid stream. While the respective boiling points of TNM and nitric acid differ, i.e., TNM has a boiling point of 126° C. whereas nitric acid has a boiling point around about 82° C., it is difficult to remove TNM from a nitric acid stream in an effective and cost efficient method. For example, in streams of dilute nitric acid, i.e., nitric acid having a concentration less than about 65% (65% pure $HNO_3$/35% $H_2O$), TNM can be removed via distillation only up to the point at which an azeotrope is formed between nitric acid and TNM. In streams of concentrated nitric acid, i.e., nitric acid having a concentration above about 65%, TNM cannot be distilled off despite the differences in their respective boiling points.

In the process of the present invention, concentrated sulfuric acid is added to the stream of nitric acid containing the TNM. The concentration of the sulfuric acid is typically above about 70% and preferably ranges from about 80% to about 100% or more, and more preferably from about 85% to about 95%. The concentration of the nitric acid stream is preferably at least about 60% and more preferably above 65% and most preferably between about 65% and about 80%. By adding concentrated sulfuric acid, it is possible to render the TNM removable by simple sparging with air or some other inert gas. While not wishing to be bound by theory, it is believed that the added sulfuric acid results in an increase in the vapor pressure of the TNM in the mixed acid stream. Preferably, the ratio of sulfuric acid to nitric acid is greater than about 1:1, and more preferably greater than 1.5:1 and most preferably at or above about 2:1. In fact, it has been discovered by the present inventors that mixing sulfuric acid with nitric acid in ratios of about 2:1, that a significant portion of the TNM originally present in the mixture can be driven off spontaneously from the mixture without sparging with an inert gas.

It should be understood by the skilled artisan that the concentration of sulfuric acid is dependent upon the concentration of the nitric acid stream as well as the weight ratio of sulfuric acid to nitric acid. In particular, the concentration and amount of the sulfuric acid added to the nitric acid should be sufficient to facilitate recovery of concentrated nitric acid. That is, as the concentration of the nitric acid stream goes down, the concentration and/or weight ratio of sulfuric acid should be increased.

With the proper ratios of sulfuric acid to nitric acid, the TNM may be effectively removed from the mixed acid mixture through several separation techniques ranging from simple mixing to sparging in a packed column. For purposes of the present invention where recovery and recycle of highly concentrated nitric acid is desired, it is preferred that the mixed acid is sparged with air or other inert gas in a packed distillation column. In an alternative embodiment, the acids can be mixed in a stirred tank reactor, and the vapor allowed to exit the vessel.

Depending upon the ratio of sulfuric acid to nitric acid in the mixed acid stream, the separation of TNM can be effectively performed over a wide range of temperatures, preferably from about 40° C. to about 80° C. More preferably, the separation to TNM is performed at a temperature from about 60° C. to about 80° C.

As used herein, the term "substantially organic-free" in regard to a inorganic process stream, e.g., an inorganic acid stream, means that the inorganic process stream contains less than 5 percent by weight, preferably less than 2 percent by weight, and most preferably less than 1.0 percent by weight, of organic compounds.

Proper separation according to the above produces an overhead stream that contains a substantial portion of the TNM that is being generated in the nitric acid streams. The additional benefit of this type of clean mixed acid separation is that very small amounts of nitric acid are removed overhead along with the TNM as compared to the techniques of the prior art.

In a preferred embodiment, the TNM separated from the mixed acid feed stream is subsequently destroyed. The TNM can be destroyed by any techniques known to those skilled in the art, for example, Japanese Patent No. 57/156445, Sep. 27, 1982, described the destruction of tetranitromethane in a stream of nitric acid and oxides of nitrogen (NOx) by absorption of the stream into 25% aqueous sodium hydroxide. Tetranitromethane has also been converted to nitroform by radiolysis techniques (Yamato, O. *Int. J. Radiat. Biol. Relat. Stud. Phys.*, Chem. Med. 1982, 42 (6), 661; Sutton, H. C.; Seddon, W. A.; Sopchyshyn, F. C. *Can. J. Chem.* 1978, 56, 1961; and Sutton, H. C. *J. Chem. Soc. Faraday I* 1975, 71, 2142.) (i.e. 0.5µ electron pulses) or reaction with sodium hydroxide in the presence of aqueous hydrogen peroxide (see, Brown, L. H.; Geckler, R. D., "Research in Nitropolymers and their Application to solid smokeless Propellants," Aerojet Engrg. Corp. quarterly Summary Report 371, contr NFomr-462 (15 Apr. 1949); Harada, T.; Nishikido, N.; Morio, Y; Matuura, R. *Bull. Chem. Soc. Jpn.* 1981, 4 (9), 2592; and Mundy, R. A.; Gilbert, E. E. Report RAD-240.10, PI-557, ARLCD-TR-78027, AD-E400164. Order No. AD-A056244, Gov. Rep. Announce. Index (U.S.) 1978, 78 (21), 250). Tetrranitromethane has been decomposed photochemically in the presence and absence of organic materials (see Isacs, N. S.; Abed, O. H. *Tet. Lett.* 1982, 23, 2799; Slovelskii, V. I.; Bolykin, V. P. *Izu. Akad. Nauk SSR, Ser. Khim.* 1975, 10, 2186; and Frank, A. J.; Henglein, A. *Berichte der Bunsen Gesellschaft* 1976, 7, 393.) Tetrranitromethane has been converted to trinitromethane by treatment with $C_2O_4$ radical anions (see Kimura, M.; Ikeda, T.; Hara, N. *Nippon Kagaku Karshi* 1982, 3, 341.). Tetranitromethane has been reduced to trinitromethane by direct reaction with thiosulfate ($S_2O_3^{2-}$) and by the reaction with copper I formed in the reaction of copper II with thiosulfate ($S_2O_3^{2-}$) (see Kimura, M.; Skukutani, M. *Bull. Chem. Soc. Jap.* 1979, 52, 2535; Okhlobystina, L. V.; Cherkasova, T. I. *Izu. Akad. Nauk SSSR, Ser. Khim.* 1975, 10, 2381.). Tetranitromethane has been electrochemically reduced (see Korsakov, V. G.; Kedrinskii, I. A. *Elektrokhimiya* 1976, 12, 1562.). Frank and Henglein have noted the solvolysis of tetranitromethane to trinitromethane in aqueous (pH=5–7) and nonaqueous systems. TNM can also be effectively destroyed through pyrolysis (see U.S. Pat. No. 4,713,232)

The solubility of tetranitromethane in dilute nitric acid is limited (e.g., 0.55% by weight at 40° C. in 40% nitric acid). This increases the possibility for tetranitromethane to phase separate from dilute nitric acid. This would create a hazardous situation if the TNM were to concentrate in the presence of an organic material also in the system to create a detonable mixture.

Quite surprisingly, it was also discovered by the present inventors that TNM can be effectively destroyed in dilute nitric acid (e.g., about 40% or below). It is not uncommon for TNM to be generated in processes which employ dilute nitric acid streams. Traditional separation methods such as distillation fail to remove sufficient amounts of TNM because TNM co-distills with dilute nitric acid. However, it was unexpectedly observed that TNM decomposes in dilute nitric acid when heated to between about 40° C. and about 100° C.

Accordingly, it is contemplated by the present invention that the TNM which is separated by the above methods can be destroyed by adjusting the nitric acid concentration level of the TNM containing nitric: acid stream to between about 1% and about 45% and by heating the dilute nitric acid stream to a temperature sufficient to destroy the TNM. As indicated above, temperatures between about 40° C. and about 100° C. will be sufficient. More preferably, the dilute nitric acid ranges from about 20% to about 40% and most preferably from about 30% to about 40% in strength. The temperature is increased up to 90° C. or higher depending on the rate at which it is desired to destroy the TNM. It will be understood by the skilled artisan that both the nitric acid concentration level and temperature are somewhat interdependent and can be adjusted within a slightly broader range and still effectively destroy the TNM.

The present inventors further discovered that the addition of certain chemicals such as sodium nitrite can increase the rate at which the TNM is destroyed in the dilute nitric acid. Other chemicals which can increase the rate at which TNM is destroyed in dilute nitric acid include oxides of nitrogen (NOx) such as $NO_2$, NO, $N_2O_3$, etc.

The process of the present invention allows for the efficient recovery of concentrated nitric acid, e.g., up to 99%. For example, the mixed acid stream can be sent to a separation unit where concentrated nitric acid is distilled overhead and weak sulfuric acid is a bottoms product. The concentrated nitric acid is able to be recycled directly back into the nitration process with a portion of the TNM removed and very little of the nitric acid being lost in the process. The weak sulfuric acid can be concentrated by boiling off water to obtain reconstituted strong sulfuric acid which can then be continuously be revised to mix with TNM contaminated nitric acid.

EXAMPLES

Standard laboratory equipment was used to conduct the solubility and solvolysis studies as well as the sparging experiments. TNM was analyzed by high pressure liquid chromatography using a Waters Resolve C18 5-micron Radial-Pak column, an isocratic solvent gradient using 50/50 acetonitrile/water, 2.0 milliliters/minute, and UV detection at 280 nanometers. Acid samples were diluted with acetonitrile prior to analysis. Residence times are reported in hours (h) and TNM levels are reported in parts per million (ppm), unless otherwise noted below.

Example 1

A. Destruction of TNM in 40% Nitric Acid at 25°–60° C.

The destruction of TNM was first evaluated on a nitration process that produced 4-nitro-N-methylphthalimide (NPI). The process included the nitration of N-methylphthalimide (PI) with 99% nitric acid (1% by weight water) in a continuous process to produce NPI. A byproduct of the nitration, 3,5-dinitro-3-hydroxy-N-methylphthalimide, decomposed under the reaction conditions in the nitrators and devolitilizing equipment to produce TNM. It is estimated that ~8 pounds/hours of TNM was generated in the nitrators and devolitilizing equipment. It was important in the nitration process not to exceed the solubility limit of TNM in the acid streams as potentially dangerous mixtures could result.

A portion of the TNM generated was contained within an intermediate process mixture of NPI in 35–40% nitric acid. It was found that the TNM in the intermediate mixture was destroyed within several hours at 25°–60° C.

B. Destruction of TNM in 40% Nitric Acid at 90° C.

A 5 milliliter (mL), screw-top tube was charged with 2.0 mL of 40% nitric acid, 11.46 milligram (mg) of tetranitromethane, and an internal standard (dinitrobenzene). The tube was sealed with a inert fluoropolymer lined cap. The tube was heated to 90° C. and periodically sampled to determine the level of tetranitromethane and trinitromethane. The results are shown below (Table I).

TABLE I

Stability of Tetranitromethane in 40% Nitric Acid at 90° C.

| Time (h) | Tetranitromethane (ppm) | Trinitromethane (ppm) |
|---|---|---|
| 0 | 4597 | 0 |
| 2.5 | 2592 | 266 |
| 21.5 | 706 | 802 |
| 43.5 | 277 | 1055 |

As can be seen from Example 1B, TNM was effectively destroyed by substantially clean 40% nitric acid at 90° C.

C. Destruction of TNM in 40% Nitric Acid at 90° C. in the Presence of Sodium Nitrite A 5-mL screw-top tube was charged with 2.0 mL of 40% nitric acid, 11.46 mg of TNM, 108 mg of sodium nitrite, and dinitrobenzene. The tube was sealed and heated to 90° C. The tube was sampled and the level of TNM determined; the results appear in Table II.

TABLE II

Stability of Tetranitromethane in 40% Nitric Acid at 90° C. In the Presence of Sodium Nitrite

| Time (h) | Tetranitromethane (ppm) |
|---|---|
| 0 | 5000 |
| 1 | 1331 |
| 1.67 | 675 |
| 5 | 238 |

The level of trinitromethane at 5 hours was less than 50 ppm.

D. Destruction of Trinitromethane in 40% Nitric Acid at 90° C. in the Presence of Sodium Nitrite A 5-mL screw-top tube was charged with 2.0 mL of 40% nitric acid, 14.7 mg of trinitromethane, 104 mg of sodium nitrite, and dinitrobenzene. The tube was sealed and heated to 90° C. The tube was sampled and the level of trinitromethane was determined; the results appear in Table III.

TABLE III

Stability of Tetranitromethane in 40% Nitric Acid at 90° C. In the Presence of Sodium Nitrite

| Time (h) | Tetranitromethane (ppm) |
|---|---|
| 0 | 5897 |
| 2 | 1003 |
| 5.5 | 76 |

E. Destruction of TNM in 40% Nitric Acid in the Presence of Nitric Oxide

This example shows accelerated decomposition of tetranitromethane in 40% nitric acid in the presence of nitric oxide. A glass reactor was charged with approximately 42 grams (g) of 40% nitric acid containing 4600 ppm by weight TNM. The glass reactor was placed under 60 pounds per square inch (psi) of nitric oxide and 50 psi of air. The glass reactor was sealed and heated at 90° C. The results are shown in Table IV below.

TABLE IV

| Time (h) | Tetranitromethane Level (ppm) |
|---|---|
| 0 | 4600 |
| 1 | 3363 |
| 4.7 | 505 |
| 7 | 416 |

Table V below shows a typical rate of disappearance of TNM in 40% nitric acid in the absence of NOx.

TABLE V

| Time (h) | Tetranitromethane Level (ppm) |
|---|---|
| 0 | 4600 |
| 1.3 | 3930 |
| 3.25 | 3170 |
| 20 | 3410 |
| 44 | 3262 |

Example 2

In this example, an inert vapor stream is used to facilitate TNM stripping from a mixture of nitric acid and sulfuric acid. A vessel was charged with 437.6 g of 86% sulfuric acid (86% pure sulfuric acid, 14% water) and 212.6 g of 70% nitric acid that contained 0.76 weight % TNM (~147.5 g pure nitric acid, ~63.5 g water, and ~1.6 g TNM). The mixture was fed to a 12"×1.5" jacketed glass column packed with glass helices. The jacket of the column was heated with the use of a hot oil recirculating unit. Air was metered into the bottom of the packing. The acid mixture was metered to the top of the column. Effluent was collected at the bottom of the column, weighed, and analyzed for TNM. The vapor off the top of the column was scrubbed in a trap containing dilute sodium hydroxide. It was shown that with an oil jacket temperature of 90° C., an air flow of 2.0 liters/minute, and an acid feed rate of 2.0 milliliters/minute (mL/min) that 90% of the TNM in the acid mixture was removed and 90% of the nitric acid was recovered as shown by analysis of the liquid collected at the bottom of the column. The missing nitric acid was lost overhead of the column.

This experiment could also be run wherein the 70% nitric acid that is contaminated with TNM is mixed with 86 % sulfuric acid just prior to or at the top of the stripping column.

Further, it was shown that with an oil jacket temperature of 90° C., an air flow rate of 1 liter/min, and an acid flow rate of 1.7 mL/min, that 90% of the TNM in the acid mixture was removed and 97% of the nitric acid was recovered as shown by analysis of the liquid collected at the bottom of the column.

Further it was shown that with an oil jacket temperature of 90° C., and air flowrate of 3 liters/min, and an acid flow rate of 2.0 mL/min that 100% of the TNM in the acid mixture was removed and 78% of the nitric acid was recovered as shown by analysis of the liquid collected at the bottom of the column.

The actual liquid temperature in the column was substantially below 90° C. (actual was about 40°–50° C.). In actual practice, it would be preferred to preheat the acid mixture or acid streams prior to introduction into the stripping column to ensure adequate control over the acid mixture temperature and over the rate of TNM removal. The TNM could be destroyed in weak nitric acid as in Example 1 or by other means such as pyrolysis as described in U.S. Pat. No. 4,713,232.

The acid mixture product from the stripping column can then be sent to a nitric acid concentrator/sulfuric acid concentrator (NAG SAC) unit to recover 99% nitric acid.

Example 3

TNM can be removed from 1 part strong nitric acid (60–99% by weight nitric acid, containing trace to 2% by weight TNM) by mixing it with 2 parts of >85% sulfuric acid at room temperature in a packed column or common vessel and allowing the vapor that is evolved to exit the unit operation employed. The vapor contained NOx, water, and a portion of the TNM that originally contaminated the nitric acid. The heat of mixing of 1 part 70% nitric acid (at 25° C.) with 2 parts 86% sulfuric acid (at 25° C.) resulted in a solution with a temperature of approximately 45° C. The NOx acted as the vapor stripping agent to remove a portion of the TNM. Typically, recycled 70% nitric contained approximately 1% NOx. The advantages of this method is that an inert vapor stream does not have to be employed to remove the TNM. This decreases the inert gas load on the unit operation eventually used to scrub or destroy the TNM. Additionally, the nitric acid and sulfuric acid do not have to be preheated prior to mixing, or acids, once mixed, do not require heating to remove the TNM.

The method removes 1–10% of the TNM initially present in the 70% nitric acid, depending on the design of the acid mixing unit operation. This should be sufficient to provide a potential TNM removal rate that is greater than or equal to the TNM generation rate in any particular nitration process.

This method would be applicable to at least processes which mix 65–99% nitric acid (1 part) with 85–100% sulfuric acid (2 parts). Other acid mixtures are possible as long as enough sulfuric acid is employed to eventually recover 99% nitric acid from the final acid mixture.

The TNM-containing vapor stream could be treated to destroy the TNM in several ways, including, e.g.,(a) by scrubbing the vapor with 40% nitric acid and subsequent destruction of the TNM via solvolysis; (b) by scrubbing the vapor with 40% nitric acid containing sodium nitrite wherein the sodium nitrite acts as a TNM destruction accelerating agent; (c) by scrubbing the vapor with dilute caustic to destroy the TNM; and (d) by pyrolysis.

What is claimed is:

1. A process for removing tetranitromethane from a tetranitromethane-contaminated concentrated nitric acid stream otherwise containing less than 5 percent by weight of organic compounds, comprising the steps of:

(A) adding concentrated sulfuric acid containing less than 5 percent by weight of organic compounds to said nitric acid stream to form a mixed acid stream that contains tetranitromethane, wherein the amount of sulfuric acid added is effective to render the tetranitromethane capable of removal from the mixed acid stream by sparging the mixture with air or with an inert gas, and (B) separating the tetranitromethane from the mixed acid stream.

2. The process of claim 1, wherein the amount of sulfuric acid added in step A is sufficient to create a sulfuric acid/nitric acid weight ratio of at least 1:1.

3. The process of claim 2, wherein the amount of sulfuric acid added in step A is sufficient to create a sulfuric acid/nitric acid weight ratio of at least 1.5:1.

4. The process of claim 3, wherein the amount of sulfuric acid added in step A is sufficient to create a sulfuric acid/nitric acid weight ratio of at least 2:1.

5. The process of claim 4, wherein the concentration of said nitric acid ranges from about 65% to about 100% and the concentration of said sulfuric acid ranges from about 80% to about 100%.

6. The process of claim 5, wherein the concentration of said nitric acid ranges from about 65% to about 75% and the concentration of said sulfuric acid is greater than about 85% to about 90%.

7. The process of claim 1, further comprising the step of (C) separating the nitric acid from the sulfuric acid.

8. The process of claim 7, further comprising the step of (D) increasing the concentration of the sulfuric acid and recycling said concentrated sulfuric acid to step (A).

9. The process of claim 7, further comprising the step of (E) destroying the tetranitromethane separated in step (B) by pyrolysis.

10. The process of claim 7, further comprising the step of (E) destroying the tetranitromethane separated in step (B) by caustic scrubbing.

11. The process of claim 7, further comprising the step of (E) destroying the tetranitromethane separated in step (B) by adding dilute nitric acid to said separated tetranitromethane containing stream to achieve a nitric acid concentration sufficient to destroy said tetranitromethane through heating and optionally through addition of sodium nitrite or oxides of nitrogen.

12. The process of claim 1, wherein the temperature at which said separation step (B) is performed at a temperature below the boiling point of the nitric acid.

13. The process of claim 12, wherein the temperature at which said separation step (B) is performed is below about 82° C.

14. The process of claim 13, wherein the temperature at which said separation step (B) is performed ranges from about 65° C. to about 82° C.

15. The process of claim 1, wherein said separation is achieved by separating said mixed acid stream of (A) with air, nitrogen, oxides of nitrogen, or mixtures thereof.

* * * * *